(12) United States Patent
Qiu et al.

(10) Patent No.: US 8,049,040 B2
(45) Date of Patent: Nov. 1, 2011

(54) ETHYLENE-TETRAFLUOROETHYLENE PHOSPHATE COMPOSITION

(75) Inventors: Weiming Qiu, Wilmington, DE (US); Xiuling Shirley Wang, Newark, DE (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 835 days.

(21) Appl. No.: 12/152,983

(22) Filed: May 19, 2008

(65) Prior Publication Data

US 2009/0286885 A1      Nov. 19, 2009

(51) Int. Cl.
*C07F 9/02* (2006.01)
(52) U.S. Cl. .......... 568/8; 514/52; 514/75; 514/183; 524/589; 568/11; 435/1.1
(58) Field of Classification Search ............ 260/987; 568/8, 11; 514/52, 75, 183; 524/589; 435/1.1
See application file for complete search history.

(56) References Cited

U.S. PATENT DOCUMENTS

| | | | |
|---|---|---|---|
| 2,597,702 | A | 5/1952 | Benning |
| 3,083,224 | A | 3/1963 | Brace et al. |
| 3,818,074 | A | 6/1974 | Ahlbrecht |
| 3,956,000 | A | 5/1976 | Kuhls et al. |
| 4,064,067 | A | 12/1977 | Lore |
| 4,145,382 | A * | 3/1979 | Hayashi et al. ............ 558/92 |
| 4,219,681 | A | 8/1980 | Schwenk et al. |
| 4,346,250 | A | 8/1982 | Satokawa et al. |
| 5,411,766 | A | 5/1995 | Kirchner |
| 5,714,082 | A | 2/1998 | Boardman et al. |
| 5,763,552 | A | 6/1998 | Feiring et al. |
| 6,124,386 | A | 9/2000 | Yokota et al. |
| 6,271,289 | B1 | 8/2001 | Longoria et al. |
| 2008/0113200 | A1 | 5/2008 | Peng et al. |

FOREIGN PATENT DOCUMENTS

| | | |
|---|---|---|
| DE | 3035641 | 5/1982 |
| EP | 0 633 016 B1 | 12/1999 |
| FR | 2530623 | 1/1984 |
| JP | 01271484 | 10/1989 |
| JP | 1995252447 A | 10/1995 |
| JP | 1998081873 A | 3/1998 |

OTHER PUBLICATIONS

Stefani et al. J. Am. Chem. Soc. 1961, 83, 4732-4736.*
Dolbier, W.R., Chem. Rev. 1996, 196, 1557-1584.*
Brace, N.O., J. Org. Chem., 1996, 61, 6504-6516.*

* cited by examiner

*Primary Examiner* — Jeffrey S. Lundgren
*Assistant Examiner* — Ibrahim D Bori
(74) *Attorney, Agent, or Firm* — Nancy S. Mayer

(57) ABSTRACT

Fluorophosphate containing an ethylene-tetrafluoroethylene moiety of formula (I) or (II):

$$(A)_w\text{-P(O)(O}^-\text{M}^+)_{3-w} \quad \text{(I)}$$

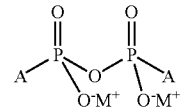

(II)

wherein
A is $R_f$—$(CH_2)_k$—$[(CF_2CF_2)_y$—$(CH_2CH_2)_z]_m$O and contains from about 8 to about 22 carbon atoms;
$R_f$ is $C_nF_{2n+1}$;
n and k are each independently 1 to about 6;
y, z, and m are each independently 1, 2, 3, or mixture thereof;
w is 1 or 2 or a mixture thereof; and
M is hydrogen, ammonium ion, an alkali metal ion, or an alkanolammonium ion,
said fluorophosphate useful as a surfactant for altering the surface behavior of a liquid by addition thereto, and for providing surface effects to a substrate treated with a composition containing the fluorophosphate.

18 Claims, No Drawings

ETHYLENE-TETRAFLUOROETHYLENE PHOSPHATE COMPOSITION

FIELD OF INVENTION

This invention relates to the field of polyfluorinated compounds and particularly to fluorophosphates containing an ethylene-tetrafluoroethylene moiety, and to their use as surfactants, and as additives for coatings.

BACKGROUND

Polyfluorinated compositions are used in the preparation of a wide variety of surface treatment materials. Various materials made from perfluorinated compositions are known to be useful as surfactants or treating agents to provide surface effects to substrates. Surface effects include repellency to moisture, soil, and stains, and other effects, which are particularly useful for fibrous substrates and other substrates such as hard surfaces. Many such surfactants and treating agents are fluorinated polymers or copolymers.

U.S. Pat. No. 3,956,000 discloses the telomerization of perfluoroethyl iodide or 1,2-diodotetrafluoroethylene with tetrafluoroethylene, and optionally with a lesser amount of chlorotrifluoroethylene, bromotrifluoroethylene, iodotrifluoroethylene, hexafluoropropylene, 1,1-difluoroethylene or ethylene, to make fluorocarbon waxes with a molecular weight of 10,000 to 200,000 by use of an emulsion process using a purely aqueous phase as the reaction media while applying specific stirring energy. Using up to 15% of telogen and at least 85% olefins is disclosed. This technology does not permit useful oligomeric iodides with a molecular weight less than 2,000. This patent does not disclose oligomerization of tetrafluoroethylene and ethylene to produce short-chain oligomeric iodides or other useful oligomeric derivatives, such as the corresponding alcohols or thiols.

Customer requirements for surfactants and for surface protection products are in a state of constant evolution, and there is a continuing need for new cost-effective, environmentally friendly chemical intermediates and products. Industry is constantly searching for compounds with minimum environmental impact and higher fluorine efficiency. In particular there is a need for surfactants and surface treatment agents containing short chain fluorochemical groups wherein some of the expensive fluorocarbon moieties have been replaced with less expensive and more readily biodegradable moieties. The present invention provides such surfactants and surface treatment agents.

SUMMARY OF INVENTION

The present invention comprises a compound comprising formula (I) or (II):

$$(A)_w\text{-P(O)(O}^-\text{M}^+)_{3-w} \quad \text{(I)}$$

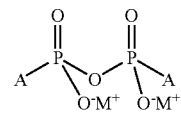
(II)

wherein

A is $R_f\text{—(CH}_2)_k\text{—[(CF}_2\text{CF}_2)_y\text{—(CH}_2\text{CH}_2)_z]_m\text{O}$ and contains from about 8 to about 22 carbon atoms;

$R_f$ is $C_nF_{2n+1}$;

n and k are each independently 1 to about 6;

y, z, and m are each independently 1, 2, 3, or mixture thereof;

w is 1 or 2 or a mixture thereof; and

M is hydrogen, ammonium ion, an alkali metal ion, or an alkanolammonium ion.

The present invention further comprises method of altering the surface behavior of a liquid comprising adding to the liquid a compound of formula (I) or (II) or a mixture thereof.

The present invention further comprises a method of providing resistance to blocking and leveling to a substrate having deposited thereon a coating composition comprising adding to the coating composition, prior to deposition on the substrate, a composition comprising one or more compounds of formula (I) or (I) or a mixture thereof.

The present invention further comprises a substrate to which has been applied a composition comprising one or more compounds of formula (I) or (II) or a mixture thereof.

DETAILED DESCRIPTION OF INVENTION

Hereinafter trademarks are designated by upper case.

The present invention comprises fluorinated aqueous compounds useful as surfactants or as surface treatment agents to impart surface properties to substrates treated therewith. The compounds of the present invention are also useful as additions to liquids and coating compositions to impart certain surface properties to substrates coated with such compositions. Other embodiments of the invention include a method of treating substrates to impart surface effects, and substrates having improved surface properties.

The present invention comprises compounds of formula (I) or (II):

$$(A)_w\text{-P(O)(O}^-\text{M}^+)_{3-w} \quad \text{(I) or}$$

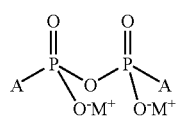
(II)

wherein

A is $R_f\text{—(CH}_2)_k\text{—[(CF}_2\text{CF}_2)_y\text{—(CH}_2\text{CH}_2)_z]_m\text{O}$ and contains from about 8 to about 22 carbon atoms;

$R_f$ is $C_nF_{2n+1}$;

n and k are each independently 1 to about 6;

y, z, and m are each independently 1, 2, 3, or mixture thereof;

w is 1 or 2 or a mixture thereof; and

M is hydrogen, ammonium ion, an alkali metal ion, or an alkanolammonium ion.

One embodiment of the invention is a composition of formula (I) or (II) wherein $R_f$ has 2 to 6 carbon atoms, preferably 2 to 4 carbon atoms, and y, z and m are each 1 to 2, preferably each 1. Other particular embodiments are compositions wherein M is an ammonium or an alkanolammonium ion. Another embodiment of the invention comprises a mixture of a mono(fluoroalkyl) phosphate of formula (I), wherein w is 1, of about 15 to 80 mol %, and a bis(fluoroalkyl) phosphate of formula (I) wherein w is 2, of about 20 to about 85 mol %. These particular compositions are useful in all other embodiments of the invention, including methods of application, and treated substrates, discussed herein.

The fluoroalkylphosphates of formula (I) and (II) are prepared according to the method described by U.S. Pat. Nos.

4,064,067 and 2,597,702 using a phosphorus pentoxide route, or by U.S. Pat. Nos. 6,271,289 and 3,083,224 using a phosphorus oxychloride route, each herein incorporated by reference. Typically, either phosphorus pentoxide ($P_2O_5$) or phosphorus oxychloride ($POCl_3$) is reacted with the fluoroalkyl alcohol or fluoroalkyl thiol to give mixtures of the mono- and bis(fluoroalkyl)phosphoric acids. Neutralization, using common bases such as ammonium or sodium hydroxides, or alkanol amines, for instance, diethanolamine (DEA), provides the corresponding phosphates. Reacting an excess of fluoroalkyl alcohol or fluoroalkyl thiol with $P_2O_5$ followed by neutralization provides a mixture of mono(fluoroalkyl)phosphate and bis(fluoroalkyl)phosphate. The corresponding phosphite and phosphinate compositions are prepared in a similar manner.

The resulting composition is then diluted with water, mixture of water and solvent, or further dispersed or dissolved in a solvent selected from the groups comprising simple alcohols and ketones that are suitable as the solvent for final application to substrates (hereinafter the "application solvent"). Alternatively, an aqueous dispersion, made by conventional methods with surfactants, is prepared by removing solvents by evaporation and the use of emulsification or homogenization procedures known to those skilled in the art. Such solvent-free emulsions may be preferred to minimize flammability and volatile organic compounds (VOC) concerns. The final product for application to a substrate can be a dispersion, if water based, or a solution.

Specific fluorinated alcohols useful in the preparation of the phosphate compounds of the present invention are listed in Table 1.

TABLE 1

| Compound No. | Structure |
|---|---|
| 1. | $C_2F_5CH_2CH_2CF_2CF_2CH_2CH_2OH$, |
| 2. | $C_2F_5CH_2CH_2(CF_2CF_2)_2CH_2CH_2OH$, |
| 3. | $C_2F_5(CH_2CH_2)_2CF_2CF_2CH_2CH_2OH$, |
| 4. | $C_2F_5CH_2CH_2CF_2CF_2(CH_2CH_2)_2OH$, |
| 5. | $C_2F_5CH_2CH_2(CF_2CF_2CH_2CH_2)_2OH$, |
| 6. | $C_2F_5(CH_2CH_2)_2(CF_2CF_2CH_2CH_2)_2OH$, |
| 7. | $C_2F_5(CH_2CH_2)_2CF_2CF_2)_2(CH_2CH_2)_2OH$, |
| 8. | $C_2F_5CH_2CH_2(CF_2CF_2)_3CH_2CH_2OH$, |
| 9. | $C_2F_5CH_2CH_2CF_2CF_2(CH_2CH_2)_2CF_2CF_2CH_2CH_2OH$, |
| 10. | $C_2F_5(CH_2CH_2)_2(CF_2CF_2)_2CH_2CH_2OH$, |
| 11. | $C_4F_9CH_2CH_2CF_2CF_2CH_2CH_2OH$, |
| 12. | $C_4F_9CH_2CH_2(CF_2CF_2)_2CH_2CH_2OH$, |
| 13. | $C_4F_9(CH_2CH_2)_2CF_2CF_2CH_2CH_2OH$, |
| 14. | $C_4F_9CH_2CH_2CF_2CF_2(CH_2CH_2)_2OH$, |
| 15. | $C_4F_9CH_2CH_2(CF_2CF_2CH_2CH_2)_2OH$, |
| 16. | $C_4F_9(CH_2CH_2)_2(CF_2CF_2CH_2CH_2)_2OH$, |
| 17. | $C_4F_9(CH_2CH_2)_2(CF_2CF_2)_2(CH_2CH_2)_2OH$, |
| 18. | $C_4F_9CH_2CH_2(CF_2CF_2)_3CH_2CH_2OH$, |
| 19. | $C_4F_9CH_2CH_2CF_2CF_2(CH_2CH_2)_2CF_2CF_2CH_2CH_2OH$, |
| 20. | $C_4F_9(CH_2CH_2)_2(CF_2CF_2)_2CH_2CH_2OH$, |
| 21. | $C_6F_{13}CH_2CH_2CF_2CF_2CH_2CH_2OH$, |
| 22. | $C_6F_{13}CH_2CH_2(CF_2CF_2)_2CH_2CH_2OH$, |
| 23. | $C_6F_{13}(CH_2CH_2)_2CF_2CF_2CH_2CH_2OH$, |
| 24. | $C_6F_{13}CH_2CH_2CF_2CF_2(CH_2CH_2)_2OH$, |
| 25. | $C_6F_{13}CH_2CH_2(CF_2CF_2CH_2CH_2)_2OH$, |
| 26. | $C_6F_{13}(CH_2CH_2)_2(CF_2CF_2CH_2CH_2)_2OH$, |
| 27. | $C_6F_{13}(CH_2CH_2)_2(CF_2CF_2)_2(CH_2CH_2)_2OH$, |
| 28. | $C_6F_{13}CH_2CH_2(CF_2CF_2)_3CH_2CH_2OH$, |
| 29. | $C_6F_{13}CH_2CH_2CF_2CF_2(CH_2CH_2)_2CF_2CF_2CH_2CH_2OH$, |
| 30. | $C_6F_{13}(CH_2CH_2)_2(CF_2CF_2)_2CH_2CH_2OH$. |

Specific fluorinated thiols useful in forming compounds of the invention include those analogous to the alcohols listed above in Table 1A, but having an SH in place of the OH.

The alcohols used in the preparation of the compounds of formula (I) and (II) of the present invention are prepared from the corresponding oligomeric iodides using an oleum treatment and hydrolysis. It has been found, for example, that reacting with oleum (15% $SO_3$) at about 60° C. for about 1.5 hours, followed by hydrolysis using an iced dilute $K_2SO_3$ solution, and then followed by heating to about 100° C. for about 30 minutes gives satisfactory results. But other reaction conditions can also be used. After being cooled to ambient room temperature, a solid is precipitated, isolated and purified. For example, the liquid is then decanted and the solid is dissolved in ether and washed with water saturated with NaCl, dried over anhydrous $Na_2SO_4$, and concentrated and dried under vacuum. Other conventional purification procedures can be employed.

Alternatively, the alcohols used in the preparation of the compounds of the present invention can be prepared by heating oligomeric iodides ($C_nF_{2n+1}C_2H_4$ I, $C_nF_{2n+1}CH_2$ I or $C_nF_{2n+1}$I) with N-methylformamide to about 150° C. and holding for about 19 hours. The reaction mixture is washed with water to give a residue. A mixture of this residue with ethanol and concentrated hydrochloric acid is gently refluxed (at about 85° C. bath temperature) for about 2.5 hours. The reaction mixture is washed with water, diluted with dichloromethane, and dried over sodium sulfate. The dichloromethane solution is concentrated and distilled at reduced pressure to give the alcohol. Optionally N,N dimethylformamide can be used instead of N-methylformamide. Other conventional purification procedures can also be employed.

The thiols used in the preparation of the compounds of the present invention $C_nF_{2n+1}$ $(CH_2)_x[(CF_2CF_2)_y(CH_2CH_2)_z]_m$ SH, wherein m, n, x, y, and z are as described above for formula (I), are prepared from the oligomeric iodides ($C_nF_{2n+1}$ $C_2H_4$ I, $C_nF_{2n+1}CH_2$ I or $C_nF_{2n+1}$I) by the reaction with thiourea followed by hydrolysis of the thiouronium salt as per the literature procedure (Rondestvedt, C. S., Jr.; Thayer, G. L., Jr. J. Org. Chem. 1977, 42, 2680). The oligomeric iodides are typically refluxed with thiourea in ethanol for about 36 hours and hydrolyzed using sodium hydroxide to obtain the corresponding oligomeric thiols. Alternatively, displacement reaction using NaSH in ethanol could be used to effect this transformation.

The iodides used in the preparation of the alcohols and thiols described above compounds are preferably prepared by oligomerization of $C_nF_{2n+1}C_2H_4$ I, $C_nF_{2n+1}CH_2$ I or $C_nF_{2n+1}$I using a mixture of ethylene (ET) and tetrafluoroethylene (TFE). The reaction can be conducted at any temperature from room temperature to about 150° C. with a suitable radical initiator. Preferably the reaction is conducted at a temperature of from about 400 to about 100° C. with an initiator which has about a 10 hour half-life in that range. The feed ratio of the starting materials in the gas phase, that is the moles of $C_nF_{2n+1}C_2H_4$ I, $C_nF_{2n+1}CH_2$ I or $C_nF_{2n+1}$I vs the combined moles of ethylene and tetrafluoroethylene, can be used to control conversion of the reaction. This mole ratio is from about 1:3 to about 20:1, preferably from about 1:2 to about 5:1 The mole ratio of ethylene to tetrafluoroethylene is from about 1:10 to about 10:1, preferably from about 3:7 to about 7:3, and more preferably from about 4:6 to about 6:4.

It will be apparent to one skilled in the art that many changes to any or all of the procedures described above may also be used to optimize the reaction conditions for obtaining maximum yield, productivity or product quality.

The present invention comprises fluorinated aqueous mixtures comprising a mixture of an anionic aqueous compound of formula (I) or (II) neutralized with a base, preferably an amine such as dialkanolamine base. The composition is neutralized to a pH of about 5 to about 10, preferably about 6 to about 9 and most preferably, from about 6 to about 8.

The various molar ratios of the fluoroalcohol or fluorothiol, acid, and base can be identified by the format (a:1:b): thus the (2:1:1) salt is, for example, the bis(fluoroalkyl) phosphate amine salt, the (1:1:2) salt is, for example, the fluoroalkyl phosphate bis(amine salt) and the (1:1:1) salt is, for example, the fluoroalkyl phosphate amine salt. Preferably the (2:1:1) salt is the bis(fluoroalkyl) phosphate diethanolamine salt, the (1:1:2) salt is the fluoroalkyl phosphate bis(diethanolamine salt) and the (1:1:1) salt is the fluoroalkyl phosphate diethanolamine salt.

The product of the reaction is a fluorinated sulfonate surfactant which lowers surface tension and provides improved surface effects such as blocking resistance, enhanced hiding power (leveling), spreading, wettability, penetrability, foam inhibition, dispersibility, and water and oil repellency. These improved surface effects are advantageous in many industrial applications including aqueous coatings such as inks, paints, varnishes, and the like.

The present invention further comprises a method of lowering surface tension of a medium, typically a liquid, comprising adding to the medium a compound of Formula (I), (II), or a mixture thereof, as described above. The surfactants of the present invention are effective in lowering the surface tension of a wide variety of media. Examples of suitable medium include, for example, a coating composition, latex, polymer, floor finish, ink, emulsifying agent, foaming agent, release agent, repellency agent, flow modifier, film evaporation inhibitor, wetting agent, penetrating agent, cleaner, grinding agent, electroplating agent, corrosion inhibitor, etchant solution, soldering agent, dispersion aid, microbial agent, pulping aid, rinsing aid, polishing agent, personal care composition, drying agent, antistatic agent, floor polish, or bonding agent. Adding a composition of the present invention to the medium results in lowering the surface tension of the medium due to the surfactant properties of the composition of the present invention. The composition of the present invention is typically simply blended with or added to the medium. These surfactants are especially suitable for lowering the surface tension of water, aqueous solutions, and aqueous emulsions. A low concentration of less than about 0.01% by weight of a compound of Formula (I) or (II) in the liquid is effective. The amphoteric nature of the surfactant of Formula (I) or (II) of the present invention results in it being effective across a broad pH range. Preferably the pH is greater than about 4.

The present invention further comprises a method of altering the surface behavior of a liquid comprising adding to the liquid a compound of Formula (I) or (II) as defined above. A wide variety of surface behaviors is included. Examples are wetting, penetration, spreading, leveling, flowing emulsification, stabilizing and dispersion in the wet liquids. Other examples include antiblocking, repellency and releasing in a dried coating composition on a treated substrate. Consequently, the surfactants of Formula (I) or (II) are useful in a wide variety of end use applications.

The present invention further comprises a method of providing surface properties to a substrate having deposited thereon a coating composition comprising adding to the coating composition, prior to deposition on the substrate, a composition of the above formula (I) or (II) or mixtures thereof. The compound of Formula (I) or (II) of the present invention is suitable for the use in coatings, paint, pigment, varnishes, finishing agents, floor waxes or finishes, inks and dyes. Surface effects provided include enhanced hiding power, leveling, antiblocking, anticratering, control of soiling, water and oil repellency, wetting, dispersion, blocking resistance, color development, and to combat pigment flotation problems.

Particular coating compositions suitable for use with the surfactants of the present invention, referred to herein by the term "coating base", include a composition, typically a liquid formulation, of an alkyd coating, Type I urethane coating, unsaturated polyester coating, or water-dispersed coating, and is applied to a substrate for the purpose of creating a lasting film on the substrate surface. These are conventional paints, stains, and similar coating compositions.

By the term "alkyd coating" as used herein is meant a conventional liquid coating based on alkyd resins, typically a paint, clear coating, or stain. The alkyd resins are complex branched and cross-linked polyesters containing unsaturated aliphatic acid residues. Conventional alkyd coatings utilize, as the binder or film-forming component, a curing or drying alkyd resin. Alkyd resin coatings contain unsaturated aliphatic acid residues derived from drying oils. These resins spontaneously polymerize in the presence of oxygen or air to yield a solid protective film. The polymerization is termed "drying" or "curing" and occurs as a result of autoxidation of the unsaturated carbon-carbon bonds in the aliphatic acid component of the oil by atmospheric oxygen. When applied to a surface as a thin liquid layer of formulated alkyd coating, the cured films that form are relatively hard, non-melting, and substantially insoluble in many organic solvents that act as solvents or thinners for the unoxidized alkyd resin or drying oil. Such drying oils have been used as raw materials for oil-based coatings and are described in the literature.

By the term "urethane coating" as used hereinafter is meant a conventional liquid coating based on Type I urethane resins, typically a paint, clear coating, or stain. Urethane coatings typically contain the reaction product of a polyisocyanate, usually toluene diisocyanate, and a polyhydric alcohol ester of drying oil acids. Urethane coatings are classified by ASTM D-1 into five categories. Type I urethane coatings contain a pre-reacted autoxidizable binder as described in Surface Coatings Vol. 1, previously cited. These are also known as uralkyds, urethane-modified alkyds, oil-modified urethanes, urethane oils, or urethane alkyds, are the largest volume category of polyurethane coatings and include paints, clear coatings, or stains. The cured coating is formed by air oxidation and polymerization of the unsaturated drying oil residue in the binder.

By the term "unsaturated polyester coating" as used hereinafter is meant a conventional liquid coating based on unsaturated polyester resins, dissolved in monomers and containing initiators and catalysts as needed, typically as a paint, clear coating, or gel coat formulation. Unsaturated polyester resins contain as the unsaturated prepolymer the product obtained from the condensation polymerization of a glycol such as 1,2-propylene glycol or 1,3-butylene glycol with an unsaturated acid such as maleic (or of maleic and a saturated acid, e.g., phthalic) in the anhydride form. The unsaturated prepolymer is a linear polymer containing unsaturation in the chain. This is dissolved in a suitable monomer, for instance styrene, to produce the final resin. The film is produced by copolymerization of the linear polymer and monomer by means of a free radical mechanism. The free radicals can be generated by heat, or more usually by addition of a peroxide, such as benzoyl peroxide, separately packaged and added before use. Such coating compositions are frequently termed "gel coat" finishes. For curing coatings at room temperature, the decomposition of peroxides into free radicals is catalyzed by certain metal ions, usually cobalt. The solutions of peroxide and cobalt compound are added separately to the mix and well stirred before application. The unsaturated polyester resins that cure by a free radical mechanism are also suited to irradiation curing using, for instance, ultraviolet light. This form of cure, in which no heat is produced, is particularly suited to films on wood or board. Other radiation sources, for instance electron-beam curing, are also used.

By the term "water-dispersed coatings" as used herein is meant coatings intended for the decoration or protection of a substrate composed of water as an essential dispersing component such as an emulsion, latex, or suspension of a film-forming material dispersed in an aqueous phase. "Water-dispersed coating" is a general classification that describes a number of formulations and includes members of the above described classifications as well as members of other classifications. Water-dispersed coatings in general contain other common coating ingredients. Water-dispersed coatings are exemplified by, but not limited to, pigmented coatings such as latex paints, unpigmented coatings such as wood sealers, stains, and finishes, coatings for masonry and cement, and water-based asphalt emulsions. A water dispersed coating optionally contains surfactants, protective colloids and thickeners, pigments and extender pigments, preservatives, fungicides, freeze-thaw stabilizers, antifoam agents, agents to control pH, coalescing aids, and other ingredients. For latex paints the film forming material is a latex polymer of acrylate acrylic, vinyl-acrylic, vinyl, or a mixture thereof. Such water-dispersed coating compositions are described by C. R. Martens in "Emulsion and Water-Soluble Paints and Coatings" (Reinhold Publishing Corporation, New York, N.Y., 1965).

By the term "dried coating" as used herein is meant the final decorative and/or protective film obtained after the coating composition has dried, set or cured. Such a final film can be achieved by, for non-limiting example, curing, coalescing, polymerizing, interpenetrating, radiation curing, UV curing or evaporation. Final films can also be applied in a dry and final state as in dry coating.

Blocking is the undesirable sticking together of two coated surfaces when pressed together, or placed in contact with each other for an extended period of time. When blocking occurs separation of the surfaces can result in disruption of the coating on one or both surfaces. Thus improved resistance to blocking is beneficial in many situations where two coated surfaces need to be in contact, for example on window frames.

When used as additives to a coating base the compositions of the present invention of Formula (I),or (II) as defined above are effectively introduced to the coating base or other composition by thoroughly stirring it in at room or ambient temperature. More elaborate mixing can be employed such as using a mechanical shaker or providing heat or other methods. Such methods are not necessary and do not substantially improve the final composition. When used as an additive to latex paints, the compositions of the invention generally are added at about 0.001 weight % to about 5 weight % by dry weight of the composition of the invention in the wet paint. Preferably about from about 0.01 weight % to about 1 weight %, and more preferably from about 0.1 weight % to about 0.5 weight % is used.

Floor waxes, polishes, or finishes (hereinafter "floor finishes") are generally water based or solvent based polymer emulsions. The surfactants of Formula I of the present invention are suitable for use in such floor finishes. Commercially available floor finish compositions typically are aqueous emulsion-based polymer compositions comprising one or more organic solvents, plasticizers, coating aides, anti-foaming agents, surfactants, polymer emulsions, metal complexing agents, and waxes. The particle size range and solids content of the polymer are usually controlled to control the product viscosity, film hardness and resistance to deterioration. Polymers containing polar groups function to enhance solubility and may also act as wetting or leveling agents providing good optical properties such a high gloss and distinctness of reflected image.

Preferred polymers for use in floor finishes include acrylic polymers, polymers derived from cyclic ethers, and polymers derived from vinyl substituted aromatics. Acrylic polymers include various poly(alkyl acrylates), poly(alkyl methacrylates), hydroxyl substituted poly(alkyl acrylates) and poly(alkyl methacrylates). Commercially available acrylic copolymers used in floor finishes include, for example, methyl methacrylate/butyl acrylate/methacrylic acid (MMA/BA/MAA) copolymers; methyl methacrylate/butyl acrylate/acrylic acid (MMA/BA/AA) copolymers, and the like. Commercially available styrene-acrylic copolymers include styrene/methyl methacrylate/butyl acrylate/methacrylic acid (S/MMA/BA/MMA) copolymers; styrene/methyl methacrylate/butyl acrylate/acrylic acid (S/MMA/BA/A) copolymers; and the like. Polymers derived from cyclic ethers usually contain 2 to 5 carbon atoms in the ring with optional alkyl groups substituted thereon. Examples include various oxiranes, oxetanes, tetrahydrofurans, tetrahydropyrans, dioxanes, trioxanes, and caprolactone. Polymers derived from vinyl substituted aromatics include for example those made from styrenes, pyridines, conjugated dienes, and copolymers thereof. Polyesters, polyamides, polyurethanes and polysiloxanes are also used in floor finishes.

The waxes or mixtures of waxes that are used in floor finishes include waxes of a vegetable, animal, synthetic, and/or mineral origin. Representative waxes include, for example, carnuba, candelilla, lanolin, stearin, beeswax, oxidized polyethylene wax, polyethylene emulsions, polypropylene, copolymers of ethylene and acrylic esters, hydrogenerated coconut oil or soybean oil, and the mineral waxes such as paraffin or ceresin. The waxes typically range from 0 to about 15 weight percent and preferably from about 2 to about 10 weight percent based on the weight of the finish composition.

When used as additives to a floor finish the compositions of the present invention of Formula (I), (II), or a mixture thereof, as defined above are effectively introduced to the composition by thoroughly stirring it in at room or ambient temperature. More elaborate mixing can be employed such as using a mechanical shaker or providing heat or other methods. When used as an additive to floor finishes, the compositions of the invention generally are added at about 0.001 weight % to about 5 weight % by dry weight of the composition of the invention in the wet composition. Preferably about from about 0.01 weight % to about 1 weight %, and more preferably from about 0.1 weight % to about 0.5 weight % is used.

The compounds of Formula (I), (II) or a mixture thereof are useful in many additional applications. Examples of some applications include the following.

The compounds of the present invention are suitable for the use in fire fighting compositions, for example as a wetting agent, emulsifying agent and/or dispersion. They are also useful as a component in aqueous film forming extinguishing agents, as an additive to dry chemical extinguishing agents in aerosol-type extinguishers, and as a wetting agent for sprinkler water.

The compounds of the present invention are suitable for the use in agricultural compositions. Examples include as a wetting agent, emulsifying agent and/or dispersion agent for herbicides, fungicides, weed killers, parasiticides, insecticides, germicides, bactericides, nematocides, microbiocides, defolients, fertilizers and hormone growth regulators. Formula (I) or (II) compounds are also suitable as wetting agent for foliage, for live stock dips and to wet live stock skins; as an ingredient in sanitizing, discoloring and cleaning compositions; and in insect repellent compositions. The compounds of the present invention are also useful as a wetting agent, emulsifying agent and/or dispersion agent in the manufacture of paper and plywood veneer. The compounds of the present invention are also suitable as grease/oil repellents for paper, wood, leather, skins, metals, textiles, stone, and tiles, and as penetrant for preservative impregnation.

The compounds of the present invention are also suitable for the use as a wetting agent, emulsifying agent and/or dispersion agent for polymerization reactions, particularly polymerization of fluoromonomers. These compounds are also suitable as a latex stabilizer; as an additive for foam applications to control spreading, crawling and edge buildup; and as foaming agents, mold release agents or demolding agents; as internal antistatic agent and antiblocking agent for polyolefins; as a flow modifier for extruding hot melts to aid in the control of spreading, uniformity, anticratering; and as retarder for plasticizer migration or evaporation in the plastics and rubber industry.

The compounds of the present invention are further suitable for the use in the petroleum industry as a wetting agent for oil well treatments and drilling mud; as a film evaporation inhibitor for gasoline, jet fuel, solvents, hydrocarbons; as a lubricant or cutting oil improver to improve penetration times; as an oil spill collecting agent; and as an additive to improve tertiary oil well recovery.

The compounds of the present invention are further suitable for use in the textile and leather industries as a wetting agent, antifoaming agent, penetrating agent or emulsifying agent; or as a lubricant for textiles, nonwoven fabrics and leather treatment; for fiber finishes for spreading, and uniformity; as a wetting agent for dyeing; as a binder in nonwoven fabrics; and as a penetration additive for bleaches.

The compounds of the present invention are further suitable for the use in the mining and metal working industries, in the pharmaceutical industry, automotives, building maintenance and cleaning, in household, cosmetic and personal products, and in photography and graphic arts to provide improved surface effects.

The compositions of the present invention are useful as surfactants to modify the surface tension of liquids. This results in modification of various surface properties of the liquids. These properties are obtained using lower fluorine concentrations compared with conventional surfactants, providing improved "fluorine efficiency" in the protection of treated surfaces, or are obtained using more environmentally friendly compositions.

Test Methods

The following test methods were used in the examples herein.

Test Method 1—Blocking Resistance of Architectural Latex Paints

The test method described herein is a modification of ASTM D4946-89—Standard Test Method for Blocking Resistance of Architectural Paints, which is hereby specifically incorporated by reference.

The face-to-face blocking resistance of paints to be tested was evaluated in this test. Blocking, for the purpose of this test, is defined as the undesirable sticking together of two painted surfaces when pressed together or placed in contact with each other for an extended period of time.

The paint to be tested was cast on a polyester test panel using the applicator blade. All painted panels should be protected from grease, oil, fingerprints, dust, et cetera; surface contamination will affect blocking resistance results. Typically, results are sought at 24 hours after casting the paint. After the panels have been conditioned in the conditioned room as specified in the test method for the desired period of time, six squares (3.8 cm×3.8 cm) were cut out from the painted test panel. The cut sections (three pairs) were placed with the paint surfaces face-to-face for each of the paints to be tested. Place the cut sections (three pairs) with the paint surfaces face-to-face for each of the paints to be tested. The face-to-face specimens were in the 50° C. oven on the marble tray. A no. 8 stopper was placed on top, with the smaller diameter in contact with the specimens, and then a 1000 g weight was placed on top of the stopper. This resulted in a pressure of 1.8 psi (12,400 Pascal) on the specimens. One weight and stopper was be used for each specimen to be tested. After exactly 30 minutes, the stoppers and weights were taken off the test specimens which were removed from the oven and allowed to cool in the conditioned room for 30 minutes before determining the block resistance.

After cooling, the specimens were separated by peeling apart with a slow and steady force. The blocking resistance was rated from 0 to 10, corresponding to a subjective tack assessment (sound made upon separation of the painted specimens) or seal (complete adhesion of the two painted surfaces) as determined by the operator of the method. The specimen was put near the ear to actually hear the degree of tack. The rating system is described in Table 2B. The degree of seal was estimated from the appearance of the specimens and the fraction of the paint surfaces that adhere. Paint tearing away from the test panel backing was an indication of seal. A higher number indicates better resistance to blocking.

TABLE 2

Blocking Resistance Numerical Ratings

| Blocking Resistance Numerical Ratings | Description of the Separation | Performance Description |
| --- | --- | --- |
| 10 | no tack | perfect |
| 9 | trace tack | excellent |
| 8 | very slight tack | very good |
| 7 | slight tack | good/very good |
| 6 | moderate to slight tack | good |
| 5 | moderate tack | fair |
| 4 | very tacky - no seal | poor to fair |
| 3 | 5 to 25% seal | poor |
| 2 | 25 to 50% seal | poor |
| 1 | 50 to 75% seal | very poor |
| 0 | 75 to 100% seal | very poor |

Test Method 2—Surface Tension Measurement

Surface tension is measured using a Kruess Tensiometer, K11 Version 2.501 in accordance with the equipment instructions. The Wilhelmy Plate method is used. A vertical plate of known perimeter is attached to a balance, and the force due to wetting is measured. 10 replicates are tested of each dilution, and the following machine settings are used:

Method: Plate Method SFT
Interval: 1.0 s
Wetted length: 40.2 mm
Reading limit: 10
Min Standard Deviation: 2 dynes/cm
Gr. Acc.: 9.80665 m/s^2

Test Method 3—Wetting and Leveling Test

To test the performance of the samples in their wetting and leveling ability, the samples were added to a floor polish (RHOPLEX 3829, supplied by Rohm & Haas, Spring House, Pa., was used to prepare the final testing formulation) and applied to half of a stripped 12 inch×12 inch (30.36 cm×30.36 cm) vinyl tile. A 1% by weight solution of the surfactant to be tested was prepared by dilution in deionized water. Following the manufacturer protocols, a 100 g portion of the RHOPLEX 3829 formulation was prepared, followed by addition of 0.75 g of the 1% by weight surfactant solution, to provide a test floor polish.

The test floor polish was applied to a tile by placing 3 mL portion of the test polish in the center of the tile, and spreading from top to bottom using an applicator, and finally placing a large "X" across the tile, using the applicator. The tile was allowed to dry for 25-30 min and a total of 5 coats were applied. After each coat, the tile was rated on a 1 to 5 scale (1 being the worst, 5 the best) on the surfactant's ability to promote wetting and leveling of the polish on the tile surface. The rating was determined based on comparison of a tile treated with the floor polish that contained no added surfactant according to the following scale:

Tile Rating Scale
1 Uneven surface coverage of the film, significant streaking and surface defects
2 Visible streaking and surface defects, withdrawal of the film from the edges of the tile
3 Numerous surface defects and streaks are evident but, generally, film coats entire tile surface
4 Minor surface imperfections or streaking
5 No visible surface defects or streaks

EXAMPLES

Example 1

A 400 mL shaker tube was charged with perfluoroethylethyl iodide (PFEEI) (45 g) and VAZO 64 (1 g), a polymerization initiator available from E. I. du Pont de Nemours and Company, Wilmington, Del. After cool evacuation, ethylene (6 g) and tetrafluoroethylene (25 g) were added. The resulting mixture was heated to 80° C. for 20 hours. The unreacted perfluoroethylethyl iodide was recovered by vacuum distillation at room temperature. The remaining solid was extracted with $CH_3CN$ (3×100 mL). The $CH_3CN$ extracts were concentrated and distilled at reduced pressure to give pure iodide 1,1,2,2,5,5,6,6-octahydroperfluoro-1-iodooctane. The solid remaining after $CH_3CN$ extraction was extracted with warm tetrahydrofuran. The tetrahydrofuran extract was concentrated and dried to give pure 1,1,2,2,5,5,6,6,9,9,10,10-dodecahydroperfluoro-1-iodododecane. The solid remaining after tetrahydrofuran extraction was mainly iodides of formula $C_2F_5(CH_2CH_2CF_2CF_2)_nCH_2CH_2I$ (wherein n=3 and higher oligomers), which have very low solubility in common solvents. The products 1,1,2,2,5,5,6,6-octahydroperfluoro-1-iodooctane and 1,1,2,2,5,5,6,6,9,9,10,10-dodecahydroperfluoro-1-iodododecane were characterized by H NMR and F NMR as shown below:

1,1,2,2,5,5,6,6-octahydroperfluoro-1-iodooctane: mp 75-77° C.:
H NMR (CDCl3) 2.33 (m, 4H), 2.68 (m, 2H), 3.24 (m, 2H) ppm.
F NMR (CDCl3) −85.9 (s, 3F), −115.8 (m, 4F), −119.2 (m, 2F) ppm.
1,1,2,2,5,5,6,6,9,9,10,10-dodecahydroperfluoro-1-iodododecane: mp 125-8° C.:
H NMR (acetone-d6) 2.46 (m, 8H), 2.77 (m, 2H), 3.37 (m, 2H) ppm.
F NMR (acetone-d6) −86.7 (s, 3F), −117.1 (m, 6F), −117.3 (m, 2F), −119.5 (m, 2F) ppm.

A mixture of 1,1,2,2,5,5,6,6-octahydroperfluoro-1-iodooctane (136.91 g, 248.88 mmol) prepared as described above, and N-methylformamide (NMF) (273 mL) was heated to 150° C. for 19 hours. The reaction mixture was washed with water (4×500 mL) to give a residue. A mixture of this residue, ethanol (200 mL), and concentrated hydrochloric acid (1 mL) was gently refluxed (85° C. bath temperature) for 2.5 hours. The reaction mixture was washed with water (200 mL×2), diluted with dichloromethane (200 mL), dried over sodium sulfate overnight. The dichloromethane solution was concentrated and distilled at reduced pressure to give 1,1,2,2,5,5,6,6-octahydroperfluoro-1-octanol, 50.8 g.

A 500 mL 4-NRBF equipped with an overhead stirrer, condenser, a nitrogen inlet, and a solid addition funnel; was charged 1,1,2,2,5,5,6,6-octahydroperfluoro-1-octanol (36.8 g) prepared as described above. The flask was heated to 85° C. (bath temp) while stirring (125 rpm). Phosphorus pentoxide (8 g) was slowly added via the solid addition funnel to the flask. The reaction mixture was stirred (125 rpm) at 100° C. for 16 hours. The reaction mixture was then cooled to 86° C. and DI water (144 g, 80° C.) was added while the stirring was increased to 250 rpm. The reaction mixture was stirred for 20 minutes before ammonium hydroxide (28% ammonia, 8.1 g) was added. The reaction mixture was stirred for another 4 hours and cooled to room temperature. A gel product was obtained. The calculated solids weight: 47.1 g and calculated total water 150 g. This gave 23.9 w/w% solids for the product. Surface tension was measured using Test Method 2. The results are in Table 3.

TABLE 3

| | Surface tension in water: | | |
|---|---|---|---|
| Sample Description | Concentration w/w % | Surface Tension mN/m | Std. Dev. mN/m |
| Deionized Water | 0 | 73 | 0.1 |
| Example 1 | 0.0001 | 69.9 | 0.1 |
| Example 1 | 0.001 | 48.7 | 0.1 |
| Example 1 | 0.01 | 41.1 | 0.1 |
| Example 1 | 0.1 | 20.8 | 0.1 |

Example 2

An oligomer iodide mixture, $F(CF_2CF_2CH_2CH_2)_nI$ (wherein n=2,3 were major components in about 2:1 ratio) (46.5 g) was mixed with N-methylformamide (NMF) (273 mL) and heated to 150° C. for 19 hours. The reaction mixture was washed with water (4×500 mL) to give a residue. A mixture of this residue, ethanol (200 mL), and concentrated hydrochloric acid (1 mL) was gently refluxed (85° C. bath temperature) for 24 hours. The reaction mixture was poured into water (300 mL). The solid was washed with water (2×75 mL) and dried under vacuum (2 torr, 267 Pa) to give a solid, 24.5 g. About 2 g of product was sublimed. The total yield of oligomer alcohols was 26.5 g.

In a 250 mL 3-necked round bottom flask equipped with an overhead stirrer (stainless steel stirring rod), solid addition funnel, condenser, and nitrogen blanket charged alcohol mixture (34.9 g) prepared as described above. The oligomer alcohol was heated to 120° C. to melt the alcohol, then cooled to 100° C. Phosphorus pentaoxide (7.7 g) was added to the flask. The resulting mixture was stirred at 100° C. for 17 hours. Warm water (80° C., 176 g) was added and the resulting mixture was stirred for 10 minutes, then ammonium hydroxide (28% ammonia, 7.3 g) was slowly added. The resulting mixture was stirred for another 1.5 hours. The reaction mixture was transferred into a jar when it was still hot. The reaction flask was rinsed with hot water and the water rinse was combined with the product. The product was determined to contain 11.9 w/w% solids. Surface tension was measured using Test Method 2. Surface tension measurements used a portion of E111879-135 (11.9 w/w% solids) to make the test solutions. The results are in Table 4.

TABLE 4

| Sample Description | Concentration wt. % | Surface Tension mN/m | Std. Dev. mN/m |
|---|---|---|---|
| Deionized Water | 0 | 73.1 | 0.1 |
| Example 2 | 0.0001 | 72.8 | 0.1 |
| Example 2 | 0.001 | 71.4 | 0.1 |
| Example 2 | 0.01 | 32.6 | 0.1 |
| Example 2 | 0.1 | 22.6 | 0.1 |

Example 3

A 400 mL shaker tube was charged with perfluorobutyl-ethyl iodide (PFBEI) (75 g) and VAZO 64 (1.5 g) as in Example 1. After cool evacuation, ethylene (6 g) and tetrafluoroethylene (25 g) were added. The resulting mixture was heated to 80° C. for 20 hours. Reaction mixtures from 10 identical runs were combined and the unreacted perfluorobutylethyl iodide was recovered by vacuum distillation at room temperature. The remaining solid (648 g) was extracted with $CH_3CN$ (10×300 mL). The combined $CH_3CN$ extracts were concentrated and distilled at reduced pressure to give iodide 1,1,2,2,5,5,6,6-octahydroperfluoro-1-iododecane. The solid remaining after $CH_3CN$ extraction was mainly 1,1,2,2,5,5,6, 6,9,9,10,10-dodecahydroperfluoro-1-iodotetradecane and higher oligomers. The product 1,1,2,2,5,5,6,6-octahydroperfluoro-1-iododecane was characterized by H NMR and F NMR as shown below.

1,1,2,2,5,5,6,6-Octahydroperfluoro-1-iododecane: mp 72-74° C.:

H NMR (CDCl3) 2.36 (m, 4H), 2.69 (m, 2H), 3.25 (m, 2H) ppm.

F NMR (CDCl3) −81.5 (tt, J=10, 3 Hz, 3F), −115.3 (m, 2F), −115.7 (m, 4F), −124.7 (m, 2F), −126.4 (m, 2F) ppm.

A mixture of 1,1,2,2,5,5,6,6-octahydroperfluoro-1-iododecane (12 g) prepared as described above, and oleum (15% $SO_3$, 21 5 mL) was heated to 60° C. for 2 h. A $Na_2SO_3$ solution (4 g, in water 100 mL) was slowly added to the reaction mixture at 60° C. bath between 65° C. to 90° C. internal temperatures. The resulting mixture was heated to 90° C. for 30 min. After being cooled to room temperature, a solid was precipitated. The liquid was decanted and the solid was dissolved in ether (150 mL) and washed with $Na_2SO_3$ (1 M, 20 mL), water (2×20 mL), NaCl (sat. 20 mL), dried over anhydrous $Na_2SO_4$, concentrated and dried on vacuum to give to give a residue which was further purified by distillation to give an off-white solid 6.2 g, bp, 65-79° C. at 2 torr (267 Pa) as 1,1,2,2,5,5,6,6-octahydroperfluoro-1-decanol. The product was characterized by MS, H NMR and F NMR as shown below.

MS (m/e) 392 (M+, 0.16%), 372 (3.3%), 342 (60%), 323 (53%), 223 (29%), 95 (100%). H NMR (CDCl3) 1.58 (s, 1H), 2.36 (m, 6H), 3.97 (t, J=7 Hz, 2H) ppm. F NMR (CDCl3) −81.5 (it, J=9.5, 3 Hz, 3F), −114.1 (m, 2F), −115.4 (m, 2F), −116.0 (m, 2F), −124.8 (m, 2F), −126.4 (m, 2F) ppm.

In a 100 mL flask equipped with a stir bar, condenser and nitrogen blanket, charged under nitrogen 1,1,2,2,5,5,6,6-octahydroperfluoro-1-decanol (3 g) prepared as described above, and phosphorus pentoxide (0.56 g). The mixture was heated to 100° C. for 18 hours. The reaction mixture was cooled to 86° C. and warm water (80° C., 16.5 g) was added. The resulting mixture was stirred for 1 hour and ammonium hydroxide (ammonia 28%, 2.19 g) was added. The mixture was stirred for another hour and transferred to a jar when it was still hot. The product was calculated to contain 19.2 w/w % solids. Surface tension was measured using Test Method 2. The results are in Table 5.

TABLE 5

| Sample Description | Concentration wt. % | Surface Tension mN/m | Std. Dev. mN/m |
|---|---|---|---|
| Deionized Water | 0 | 73.1 | 0.1 |
| Example 3 | 0.0001 | 72.9 | 0.1 |
| Example 3 | 0.001 | 49 | 0.1 |
| Example 3 | 0.01 | 22.6 | 0.1 |
| Example 3 | 0.1 | 20.4 | 0.1 |

Example 4

The products of Examples 1, 2 and 3 were added, at a level of 0.015% by weight fluorophosphate, to a floor polish RHOPLEX 3829, Formulation N-29-1, available from Rohm and Haas Company, Philadelphia, Pa. The blocking was tested in accordance with Test Method 1. The floor finish with no compound of the present invention added was also tested in the same manner. The results are in Table 6.

The products of Examples 1, 2 and 3 were added at a level of 75 micrograms per gram of active ingredient to the above described floor polish. The wetting and leveling ability of the floor finish was tested in accordance with Test Method 3. The floor finish with no compound of the present invention added was also tested in the same manner. The results are in Table 7.

Comparative Example A

A commercially available surfactant available from E. I. du Pont de Nemours and Company, Wilmington, Del., which was an aqueous solution of ammonium salts of fluoroalkyl phosphate in water, prepared as described in U.S. Pat. No. 3,083,224 was employed as Comparative Example A. It was added at a level of 0.015% by weight active ingredient, to a floor polish RHOPLEX 3829, Formulation N-29-1, available from Rohm and Haas Company, Philadelphia, Pa. The blocking was tested in accordance with Test Method 1. The results are in Table 6.

TABLE 6

| Blocking | |
|---|---|
| Example | rating |
| Blank | 0 |
| Comparative A | 6.7 |
| 1 | 8 |
| 2 | 8 |
| 3 | 9 |

The data in Table 6 demonstrates that the compounds of the present invention provided superior blocking when compared to a commercially available surfactant containing a higher fluorine level.

Comparative Example B

A commercially available surfactant available from E. I. du Pont de Nemours and Company, Wilmington, Del., which was a fluoroalkyl ethoxylate prepared from a fluorinated alcohol and alkylene epoxide in a water and ethylene glycol solvent, was added at a level 75 micrograms per gram of active ingredient to a floor polish RHOPLEX 3829, Formulation N-29-1, available from Rohm and Haas Company, Philadelphia, Pa. The wetting and leveling ability of the floor finish was tested in accordance with Test Method 3. The results are in Table 7.

TABLE 7

Floor Finish: (RHOPLEX)

| Coating # | Blank | Example 1 | Example 2 | Example 3 | Comparative Example B | Dry Time (minutes) |
|---|---|---|---|---|---|---|
| 1 | 1.5 | 2 | 1.5 | 1.5 | 1.5 | 30 |
| 2 | 1.5 | 2 | 2.5 | 2.5 | 2.5 | 30 |
| 3 | 1 | 2.5 | 2.5 | 3.5 | 3.5 | 30 |
| 4 | 1 | 3.5 | 3 | 4 | 3.5 | 30 |
| 5 | 1 | 3.5 | 3.5 | 4.5 | 4 | 30 |
| Average | 1.20 | 2.70 | 2.60 | 3.20 | 3.0 | |

Surfactant was diluted to 1% fluorophosphate with deionized water and added to the floor finish at 0.75% by weight. (75 micrograms per gram active ingredient)

The data in Table 7 demonstrates that the compounds of the present invention provide comparable wetting and leveling in a floor treatment when compared to a commercially available surfactant containing a higher fluorine level.

Example 5

A one gallon reactor was charged with perfluoroethylethyl iodide (PFEEI) (1997.5 g) and lauroyl peroxide (7.9 g). After cool evacuation, ethylene and tetrafluoroethylene in a ratio of 25:75 were added until pressure reached 60 psig ($413.7 \times 10^3$ Pa). The reaction was then heated to 75° C. More ethylene and tetrafluoroethylene in a 25:75 ratio were added until total 299 g tetrafluoroethylene was added [maximum pressure reached 160 psig ($1103.2 \times 10^3$ Pa)]. Both ethylene and tetrafluoroethylene feeds were stopped. The reaction was heated at 75° C. for another 4 hours. The volatiles were removed by vacuum distillation at room temperature. A solid of oligomer ethylene-tetrafluoroethylene iodides (537 g) was obtained.

A 1 L reactor was charged with the above oligomer ethylene-tetrafluoroethylene iodides (469 g) and N-methylformamide (NMF) (490 g). The mixture was heated to 150° C. for 10 hours. The resulting product was washed twice with water (213 g) to give a residue. A mixture of this residue, ethanol (179 g), and methanesulfonic acid (8 mL) was heated to reactively distill the volatiles until reaction was driven to completion to give the crude product. The crude product was washed with sodium sulfite (aqueous 10% by weight, 95 g), and water (940 g) to give a wet product. The wet product was dried by removing water using vacuum distillation. A solid consisting of ethylene-tetrafluoroethylene oligomer alcohol (2909 g) was obtained.

$POCl_3$ (15.4 g, 0.1 mol), was added into a three-necked round bottom flask equipped with a thermometer and a magnetic stir. Isopropanol 6.0 g (0.1 mol) was added into flask slowly at room temperature. The reaction mixture was heated to 70° C. and stirred for 2 hrs. 13.43 g of light yellow liquid (A) was obtained. The above ethylene-tetrafluoroethylene oligomer alcohol (18.6 g) was heated to 80° C. and a portion (5.31 g) of the reaction mixture (A) was slowly added. After addition, the reaction mixture was heated to 95° C. and stirred for 3 hrs. Deionized water (0.21 g) was added into the flask and stirred for another 2 hrs. The reaction mixture was cooled to room temperature and 20.0 g of sticky brown colored phosphate (B) was obtained. The phosphate (B) (7.0 g) was added into another flask and heated to 95° C. Diethanolamine (2.3 g) was added and stirred for 3 hrs. to give a brown colored phosphate (8.3 g). The product was dissolved in deionized water and the surface tension was measured according to Test Method 2. The results are listed in Table 8.

Example 6

$POCl_3$ (1.53 g, 0.01 mol) and 20 mL of dry tetrahydrofuran were added into a three-necked round bottom flask equipped with a thermocouple, nitrogen inlet, and a magnetic stirrer bar. The solution was cooled to 0° C. and a solution containing 6.67 g (0.02 mol) of ethylene-tetrafluoroethylene oligomer alcohol as prepared in Example 5) and 2.53 g (0.025 mol) of triethylamine in 20 mL of dry tetrahydrofuran were slowly added into the flask. After addition, the reaction was allowed to proceed for 2 hours at 0-1° C. The reaction mixture was warmed up to ambient temperature and stirred overnight. The solids were removed by filtering and the solvent and excess of triethylamine were removed with rotovap. The resulting oil was diluted in 15 mL of tetrahydrofuran. NaOH (0.8 g, 0.02 mol) was dissolved in 1.2 mL of water and was added to the reaction mixture. The solution was stirred overnight at room temperature. The solvent was evaporated using rotovap. The resulting solids were dried at 120° C. under house-vacuum and to yield 5.3 g solid phosphate. The product was dissolved in deionized water and the surface tension was measured according to Test Method 2. The results are listed in Table 8.

Example 7

$POCl_3$ (7.7 g, 0.1 mol) was added into a three-necked round bottom flask equipped with a thermometer and a magnetic stir. Isopropanol (2.9 g, 0.048 mol) was added into flask slowly at room temperature. The reaction mixture was heated to 70° C. and stirred for 2 hrs. Ethylene-tetrafluoroethylene oligomer alcohol as prepared in Example 5 (15.7 g, 0.047 mol) was slowly added into reaction mixture at 50° C. and stirred for another three hours. The reaction mixture was heated to 80° C. and 6.5 g (0.05 mol) of 1-octanol was slowly added into the flask. After addition, the reaction mixture was heated to 95° C. and stirred for 2 hrs. Deionized water (0.37 g) was added into the flask and the contents stirred for another 2 hrs. The reaction mixture was cooled to room temperature and 23.5 g of brown wax-like solid was obtained. This compound (7.0 g) was added into a flask and heated to 95° C. Diethanolamine (2.3 g) was added and stirred for 3 hrs. 8.0 g of viscous brown liquid phosphate was obtained. The product was dissolved in deionized water and the surface tension was measured according to Test Method 2. The results are listed in Table 8.

Example 8

$POCl_3$ (1.53 g, 0.01 mol) and 20 mL of dry tetrahydrofuran were added into a three-necked round bottom flask equipped with a thermocouple, nitrogen inlet, and a magnetic stirrer bar. The solution was cooled to 0° C. and a solution containing 3.34 g (0.01 mol) of ethylene-tetrafluoroethylene oligomer alcohol as prepared in Example 5) and 2.53 g (0.025 mol) of triethylamine in 20 mL of dry tetrahydrofuran were slowly added. The reaction was allowed to proceed for 2 hours at 0-1° C. Then, a solution containing 1.3 g (0.01 mol) of octanol in 10 mL of dry tetrahydrofuran was slowly added to the reaction mixture. The reaction mixture was warmed up to ambient temperature and stirred overnight. Solids were filtered and the solvent and excess of triethylamine were evaporated using a rotovap. The resulting oil was diluted in 15 mL of tetrahydrofuran. NaOH (0.8 g, 0.02 mol) was dissolved in 1.2 mL of water and was added to the reaction mixture. The solution was stirred overnight at room temperature. The solvent was evaporated using a rotovap. The resulting solids were dried at 120° C. under house-vacuum and to yield 4.0 g of yellow solid phosphate. The product was dissolved in deionized water and the surface tension was measured according to Test Method 2. The results are listed in Table 8.

TABLE 8

| % of Phosphate in water | Surface Tension (dyne/cm) | | | |
|---|---|---|---|---|
| | Example 5 | Example 6 | Example 7 | Example 8 |
| 0.001 | 61.2 | 55.5 | 58.2 | 57.9 |
| 0.005 | 42.8 | 40.0 | 48.3 | 39.8 |
| 0.01 | 36.6 | 27.9 | 37.1 | 25.3 |
| 0.05 | 21.4 | 20.7 | 22.5 | 19.8 |
| 0.1 | 20.8 | 19.8 | 22.2 | 20.0 |

What is claimed is:

1. A composition comprising a compound of formula (I) or (II):

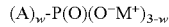 (I) or

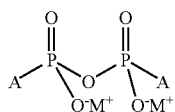 (II)

wherein
  A is $R_f$—$(CH_2)_k$—$[(CF_2CF_2)_y$—$(CH_2CH_2)_z]_m O$ and contains from 8 to 22 carbon atoms;
  $R_f$ is $C_nF_{2n+1}$;
  n and k are each independently 1 to about 6;
  y, z, and m are each independently 1, 2, 3, or mixture thereof; w is 1 or 2 or a mixture thereof; and
  M is hydrogen, ammonium ion, an alkali metal ion, or an alkanolammonium ion.

2. The composition of claim 1 wherein $R_f$ has 4 to 6 carbon atoms, and y, z and m are each 1.

3. The composition of claim 1 wherein M is an ammonium or an alkanolammonium ion.

4. The composition of claim 1 comprising a mixture of a mono(fluoroalkyl) phosphate of formula (I), wherein w is 1, in about 15 to about 80 mol %, and a bis(fluoroalkyl) phosphate of formula (I), wherein w is 2, in about 20 to about 85 mol %.

5. A method of altering the surface behavior of a liquid comprising adding to the liquid a compound of claim 1 or a mixture thereof.

6. The method of claim 5 wherein the altering the surface behavior is lowering the surface tension.

7. The method of claim 6 wherein the surface behavior is selected from the group consisting of wetting, penetrating, spreading, leveling, flowing, emulsifying, dispersing, repelling, releasing, lubricating, etching, bonding, and stabilizing.

8. The method of claim 5 wherein the liquid is coating composition, latex, polymer, floor finish, ink, emulsifying agent, foaming agent, release agent, repellency agent, flow modifier, film evaporation inhibitor, wetting agent, penetrating agent, cleaner, grinding agent, electroplating agent, corrosion inhibitor, etchant solution, soldering agent, dispersion aid, microbial agent, pulping aid, rinsing aid, polishing agent, personal care composition, drying agent, antistatic agent, floor polish, floor finish, or bonding agent.

9. The method of claim 8 wherein the liquid is a coating composition.

10. The method of claim 7 wherein the surface behavior is resistance to blocking in the coating composition after drying.

11. The method of claim 7 wherein the surface behavior is wetting and leveling during application of the coating composition to a surface.

12. The method of claim 8 wherein the liquid is a floor finish.

13. A method of providing resistance to blocking to a substrate having deposited thereon a coating composition comprising adding to the coating composition, prior to deposition on the substrate, a composition comprising one or more compounds of formula (I) or (II) or a mixture thereof:

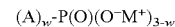 (I) or

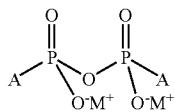 (II)

wherein
  A is $R_f$—$(CH_2)_k$—$[(CF_2CF_2)_y$—$(CH_2CH_2)_z]_m O$ and contains from 8 to 22 carbon atoms;
  $R_f$ is $C_nF_{2n+1}$;
  n and k are each independently 1 to about 6;
  y, z, and m are each independently 1, 2, 3, or mixture thereof; w is 1 or 2 or a mixture thereof; and
  M is hydrogen, ammonium ion, an alkali metal ion, or an alkanolammonium ion.

14. The method of claim 13 wherein the coating composition is a water dispersed coating, alkyd coating, Type I urethane coating, or unsaturated polyester coating.

15. The method of claim 6 or 8 wherein $R_f$ has 4 to 6 carbon atoms, and y, z and m are each 1.

16. The method of claim 6 or 8 wherein M is an ammonium or an alkanolammonium ion.

17. A substrate treated according to the method of claim 13.

18. A substrate to which has been applied a compound of claim 1.

* * * * *